United States Patent
Lee et al.

(10) Patent No.: US 9,874,533 B2
(45) Date of Patent: Jan. 23, 2018

(54) APPARATUS AND METHOD FOR MEASURING OVERALL HEAT TRANSFER COEFFICIENT

(71) Applicant: Kyungpook National University Industry-Academic Cooperation Foundation, Daegu (KR)

(72) Inventors: Hyun Woo Lee, Daegu (KR); Jong Won Lee, Daegu (KR)

(73) Assignee: Kyungpook National University Industry—Academic Cooperation Foundation, Daegu (KR)

( * ) Notice: Subject to any disclaimer, the term of this patent is extended or adjusted under 35 U.S.C. 154(b) by 552 days.

(21) Appl. No.: 14/555,848

(22) Filed: Nov. 28, 2014

(65) Prior Publication Data
US 2015/0177168 A1    Jun. 25, 2015

(30) Foreign Application Priority Data

Dec. 23, 2013  (KR) .......................... 10-2013-0161495

(51) Int. Cl.
*G01N 25/18*  (2006.01)

(52) U.S. Cl.
CPC .................. *G01N 25/18* (2013.01)

(58) Field of Classification Search
CPC ........... G01N 25/18; G01N 2011/0093; G01N 25/20; G01K 17/00
See application file for complete search history.

(56) References Cited

U.S. PATENT DOCUMENTS

| | | | | |
|---|---|---|---|---|
| 3,453,865 A | * | 7/1969 | Reiter | G01N 25/72 374/29 |
| 4,386,604 A | * | 6/1983 | Hershey | A61B 5/01 374/31 |
| 6,260,360 B1 | * | 7/2001 | Wheeler | A01N 1/02 362/371 |
| 8,215,835 B2 | * | 7/2012 | Hyde | A61B 19/026 220/592.2 |

(Continued)

FOREIGN PATENT DOCUMENTS

| | | |
|---|---|---|
| KR | 10-0520895 B1 | 10/2005 |
| KR | 10-0954197 B1 | 4/2010 |

OTHER PUBLICATIONS

Souleymane et al., "Overall Heat Transfer Coefficient Measurement of Covering Materials with Thermal Screens for Greenhouse using the Hot Box Method," *Journal of the Korean Society of Agricultural Engineers* 54(5):1-7, Sep. 2012.

*Primary Examiner* — Gail Kaplan Verbitsky
(74) *Attorney, Agent, or Firm* — Seed IP Law Group LLP (57) ABSTRACT

An apparatus for measuring an overall heat transfer coefficient may include an internal case provided using a heat insulation material and having an open upper portion, an external case configured to enclose outer sides excluding an upper portion of the internal case, and provided using a heat insulation material, a temperature adjusting portion configured to adjust an internal temperature of the external case and an internal temperature of the internal case, and a blocking portion disposed in an upper portion of the internal case to seal the internal case, in which the blocking portion may be configured to implement various covering conditions through a combination of a covering material and a thermal screen.

11 Claims, 3 Drawing Sheets

(56) References Cited

U.S. PATENT DOCUMENTS

| | | | | |
|---|---|---|---|---|
| 8,882,344 B2* | 11/2014 | Kwon | ................... | G01K 17/20 374/29 |
| 2005/0091988 A1* | 5/2005 | Stewart | ................... | B60P 3/007 62/3.1 |
| 2014/0003460 A1* | 1/2014 | Keyser | ................... | G01K 17/00 374/31 |

* cited by examiner

APPARATUS AND METHOD FOR MEASURING OVERALL HEAT TRANSFER COEFFICIENT

BACKGROUND

1. Field of the Invention

Embodiments of the present invention relate to an apparatus and method for measuring an overall heat transfer coefficient, and more particularly, to an apparatus and method for measuring an overall heat transfer coefficient that may measure a heat-retaining performance of a covering material or a thermal screen more efficiently by sealing a case.

2. Description of the Related Art

A greenhouse refers to a facility in which a cultivation space isolated from outside weather is created by covering an area with glass or a plastic film. In the greenhouse, crops are produced by artificially adjusting environments, for example, micrometeorological conditions or internal medium conditions, using a variety of supplementary equipment.

In general, an actual greenhouse may be covered with an external covering material and an internal thermal screen to minimize an external loss of heat from the greenhouse and maintain growing environment conditions, for example, a desired temperature and humidity level of the greenhouse, to be suitable for growing crops.

Heat externally lost from such a greenhouse includes convective heat, radiant heat, and conductive heat.

The convective heat refers to a transfer of heat by a temperature difference between a solid surface and a fluid. The radiant heat refers to heat produced when heat emitted from a heat source of a relatively high-temperature object passes through a space and is absorbed into a relatively low-temperature object. The conductive heat refers to a transfer of thermal energy in a solid from relatively high temperature to relatively low temperature.

However, in practice, a loss of heat by night sky radiation cooling is relatively significant in a case of a greenhouse used for agriculture.

In view of such various effects, an overall heat transfer coefficient of a covering material or a thermal screen may be measured. In this regard, Korean Patent Application No. 10-2007-0070495, filed on Jul. 13, 2007, discloses "Device for calculating convective heat transfer coefficient and method thereof".

SUMMARY

An aspect of the present invention provides an apparatus and method for measuring an overall heat transfer coefficient that may suggest a quantitative heat-retaining performance or a quantitative heat insulation performance of a covering material or a thermal screen.

Another aspect of the present invention also provides an apparatus and method for measuring an overall heat transfer coefficient that may measure an overall heat transfer coefficient more accurately by allowing heat to pass only through a blocking portion.

Still another aspect of the present invention also provides an apparatus and method for measuring an overall heat transfer coefficient that may simply implement various covering conditions of a greenhouse.

Yet another aspect of the present invention also provides an apparatus and method for measuring an overall heat transfer coefficient that may implement a wind velocity and radiation cooling.

Further another aspect of the present invention also provides an apparatus and method for measuring an overall heat transfer coefficient that may establish standards of a covering material or a thermal screen for a greenhouse.

According to an aspect of the present invention, there is provided an apparatus for measuring an overall heat transfer coefficient, the apparatus including an internal case provided using a heat insulation material and having an open upper portion, an external case configured to enclose outer sides excluding an upper portion of the internal case, and provided using a heat insulation material, a temperature adjusting portion configured to adjust an internal temperature of the external case and an internal temperature of the internal case, and a blocking portion disposed in an upper portion of the internal case to seal the internal case. The blocking portion may be configured to implement various covering conditions through a combination of a covering material and a thermal screen.

The temperature adjusting portion may include a first temperature adjusting element disposed in a space between the external case and the internal case, and a second temperature adjusting element disposed in the internal case, and the first temperature adjusting element and the second temperature adjusting element may be configured to achieve thermal equilibrium between a temperature of the space between the internal case and the external case and the internal temperature of the internal case.

The apparatus may further include a cooling portion provided on the external case, and the cooling portion may include an upper case configured to extend from an outer side of the external case, and including a side provided using a heat insulation material, and a cooler provided on the side of the upper case.

The cooler may include an upper cooler disposed on an upper side in the cooling portion, and a lower cooler disposed on a lower side in the cooling portion, and the lower cooler may be disposed adjacent to an upper portion of the blocking portion to implement a wind velocity.

The apparatus may further include a radiation cooling portion disposed on the cooling portion to implement radiation cooling.

The covering material and the thermal screen may be disposed to be spaced apart from each other in an upper portion of the internal case.

According to another aspect of the present invention, there is also provided an apparatus for measuring an overall heat transfer coefficient, the apparatus including an internal case provided using a heat insulation material, and having an open upper portion, a blocking portion disposed in an upper portion of the internal case to seal the internal case, and a cooling portion disposed on the blocking portion to circulate air above the blocking portion. The cooling portion may be configured to implement a wind velocity above the blocking portion.

The cooling portion may include a plurality of coolers, and may be configured to adjust the wind velocity by controlling the coolers.

The apparatus may further include an external case provided using a heat insulation material, and configured to seal the internal case, the blocking portion, and the cooling portion.

The apparatus may further include a temperature adjusting portion. The temperature adjusting portion may include a first temperature adjusting element disposed in a space between the external case and the internal case, and a second temperature adjusting element disposed in the internal case, and the first temperature adjusting element and the second temperature adjusting element may be configured to achieve thermal equilibrium between a temperature of the space between the internal case and the external case and an internal temperature of the internal case.

The apparatus may further include a radiation cooling portion provided on the internal case to seal the internal case, and the radiation cooling portion may be configured to implement radiation cooling.

According to still another aspect of the present invention, there is also provided a method of measuring an overall heat transfer coefficient, the method including providing an apparatus for measuring an overall heat transfer coefficient, the apparatus including an internal case provided using a heat insulation material and having an open upper portion, and an external case configured to enclose outer sides of the internal case, selecting a combination of a covering material and a thermal screen to be disposed in an upper portion of the internal case, achieving thermal equilibrium between a temperature of a space between the internal case and the external case and an internal temperature of the internal case, measuring the internal temperature of the internal case and an external temperature of an upper side of the internal case, and calculating the overall heat transfer coefficient based on the measured values.

The method may further include implementing a wind velocity or radiation cooling.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention, examples of which are illustrated in the accompanying drawings, wherein like reference numerals refer to the like elements throughout. Exemplary embodiments are described below to explain the present invention by referring to the figures.

Figure 1:
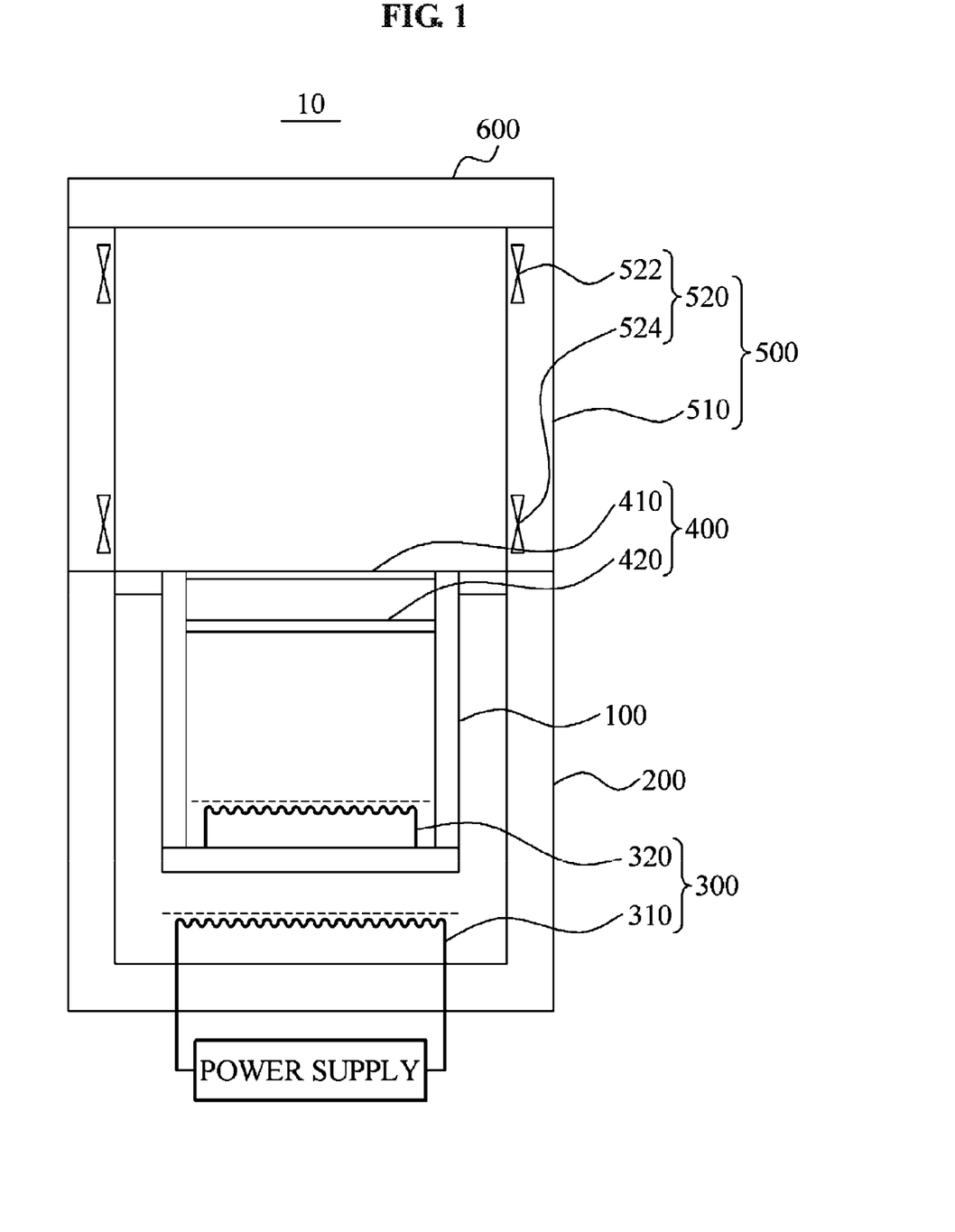
FIG. 1 is a diagram illustrating an apparatus for measuring an overall heat transfer coefficient according to an embodiment of the present invention.
Figure 2:
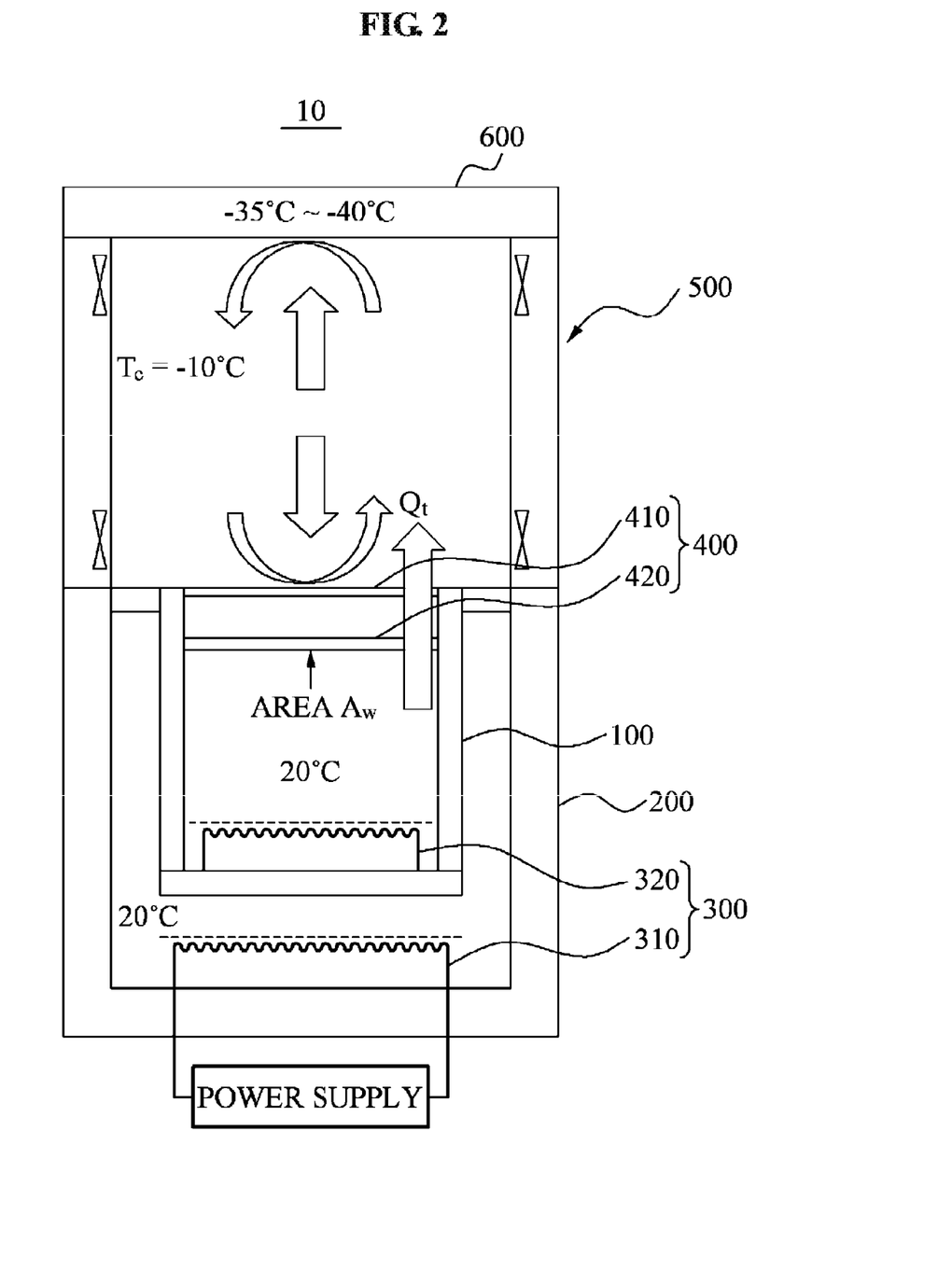
FIG. 2 is a diagram illustrating transfer of heat in an apparatus for measuring an overall heat transfer coefficient according to an embodiment of the present invention.

FIG. 1 is a diagram illustrating an apparatus 10 for measuring an overall heat transfer coefficient according to an embodiment of the present invention, and FIG. 2 is a diagram illustrating transfer of heat in the apparatus 10 for measuring an overall heat transfer coefficient according to an embodiment of the present invention.

Referring to FIG. 1, the apparatus 10 for measuring an overall heat transfer coefficient, hereinafter simply referred to as the apparatus 10, may include an internal case 100, an external case 200, a temperature adjusting portion 300, a blocking portion 400, a cooling portion 500, and a radiation cooling portion 600.

The internal case 100 may be provided using a heat insulation material, and have an open upper portion.

In detail, the internal case 100 may include four sides and a bottom.

A fixing element (not shown) may be provided on an inner side surface of the internal case 100 to dispose the blocking portion 400. For example, by inserting the blocking portion 400 into the fixing element, the blocking portion 400 may be disposed in an upper portion of the internal case 100.

In addition, the external case 200 provided using a heat insulation material may be disposed on an outer side of the internal case 100.

The external case 200 may be provided to enclose outer sides excluding the upper portion of the internal case 100.

In detail, the external case 200 may include four sides spaced apart from the four sides of the internal case 100, and a bottom spaced apart from the bottom of the internal case 100. The external case 200 may further include a top which is the same plane as a top of the internal case 100 and has a cut portion corresponding to the open upper portion of the internal case 100.

By the shape of the external case 200, the internal case 100 may be sealed in all directions, except for the open upper portion.

Thus, an outflow of internal heat of the internal case 100 or the external case 200 may be efficiently blocked.

However, the shape of the external case 200 is not limited thereto. The external case 200 may be provided in any shape to seal the internal case 100, the blocking portion 400, and the cooling portion 500.

In addition, the temperature adjusting portion 300 may be disposed in each of the internal case 100 and the external case 200.

The temperature adjusting portion 300 may include a first temperature adjusting element 310 disposed in a space between the external case 200 and the internal case 100, and a second temperature adjusting element 320 disposed in the internal case 100.

The first temperature adjusting element 310 may be disposed on the bottom of external case 200. The first temperature adjusting element 310 may include, for example, a heating coil that emits heat using electricity supplied from a power supply.

The second temperature adjusting element 320 may be disposed on the bottom of the internal case 100. Similar to the first temperature adjusting element 310, the second temperature adjusting element 320 may include, for example, a heating coil that emits heat using electricity supplied from the power supply.

For example, the first temperature adjusting element 310 may increase a temperature of the space between the external case 200 and the internal case 100, and the second temperature adjusting element 320 may increase an internal temperature of the internal case 100.

In this example, the internal temperature of the internal case 100 and the internal temperature of the external case 200 may be predetermined.

In addition, the first temperature adjusting element 310 may maintain the temperature of the space between the external case 200 and the internal case 100 to be uniform, and the second temperature adjusting element 320 may maintain the internal temperature of the internal case 100 to be uniform.

As shown in FIG. 2, the first temperature adjusting element 310 may maintain the temperature of the space between the external case 200 and the internal case 100 at 20° C., and the second temperature adjusting element 320 may maintain the internal temperature of the internal case 100 at 20° C.

Thus, the first temperature adjusting element 310 and the second temperature adjusting element 320 may achieve thermal equilibrium between the temperature of the space between the external case 200 and the internal case 100 and the internal temperature of the internal case 100.

Accordingly, heat may not be lost through the sides of the internal case 100 and thus, a loss of heat through the sides of the internal case 100 may be negligible. However, as shown in FIG. 2, the heat of the internal case 100 may be lost only through the upper portion of the internal case 100.

The blocking portion 400 may be disposed in the upper portion of the internal case 100 to seal the internal case 100.

The blocking portion 400 may include a covering material 410 and a thermal screen 420.

The covering material 410 may be detachably disposed in the internal case 100. The covering material 410 may include a polyethylene film.

The covering material 410 may prevent an outflow of heat emitted by the second temperature adjusting element 320 to an external portion of the internal case 100.

The thermal screen 420 may also be detachably disposed in the internal case 100. As shown in FIG. 1, the thermal screen 420 may be disposed below the covering material 410 to be spaced apart from the covering material 410 in a vertical direction.

Accordingly, an air layer may be formed between the covering material 410 and the thermal screen 420.

In addition, the thermal screen 420 may include a matte thermal screen or a multilayer thermal screen. Similar to the covering material 410, the thermal screen 420 may prevent an outflow of heat emitted by the second temperature adjusting element 320 to an external portion of the internal case 100.

As shown in FIG. 2, the covering material 410 and the thermal screen 420 each having an area $A_w$ may be disposed in the internal case 100.

To implement various covering conditions in the apparatus 10, various combinations of the covering material 410 and the thermal screen 420 may be used.

For example, the covering material 410 and the thermal screen 420 may be selected from among a single-covered covering material, a double-covered covering material, a single layer of a thermal screen, and two layers of a thermal screen.

As described above, the heat of the internal case 100 may be lost only through the upper portion of the internal case 100. Thus, the heat of the internal case 100 may be lost through the blocking portion 400.

Accordingly, a heat-retaining performance or a heat insulation performance of the covering material 410 or the thermal screen 420 may be measured efficiently. In addition, a heat-retaining performance or a heat insulation performance of a thin film with a thickness of 0.15 millimeters (mm) or 0.1 mm may also be measured.

The cooling portion 500 may be provided on the external case 200.

The cooling portion 500 may include an upper case 510 configured to extend from the side of the external case 200 and provided using a heat insulation material, and a cooler 520 provided on the side of the upper case 510.

An upper portion of the upper case 510 may be open or sealed, and a lower portion of the upper case 510 may be disposed adjacent to the internal case 100 based on the blocking portion 400 as a boundary.

The cooler 520 may be provided using a plurality of fans. The cooler 520 may include upper coolers 522 disposed on an upper side in the cooling portion 500, and lower coolers 524 disposed on a lower side in the cooling portion 500.

However, positions of the plurality of coolers 520 are not limited thereto. The coolers 520 may be provided at various positions.

Operations of the plurality of coolers 520 may be separately controlled. For example, all of the plurality of coolers 520 may be operated simultaneously, or only a portion of the plurality of coolers 520 may be operated. The plurality of coolers 520 may be operated using different powers.

By controlling the coolers 520, various wind velocity conditions may be adjusted. The various wind velocity conditions may include a strength of a wind velocity, and a direction of a wind velocity.

In detail, as shown in FIG. 2, the lower coolers 524 may be disposed adjacent to the top of the blocking portion 400 to implement a wind velocity by inducing a circulation of air above the blocking portion 400.

In this example, the lower coolers 524 may be provided on both sides to face each other. When only the lower cooler 524 disposed on the left side is operated, the wind velocity may head for the right side, and the wind velocity with a strength corresponding to the power of the lower cooler 524 disposed on the left side may be generated.

The upper coolers 522 may be provided on both sides to face each other. The upper coolers 522 may be disposed on the upper side in the cooling portion 500 to induce a circulation of air in the upper portion of the cooling portion 500.

For example, as shown in FIG. 2, the air directed toward the upper side by the lower coolers 524 may be induced to head for the lower side again.

Accordingly, heat may be exchanged within the cooling portion 500 by the lower coolers 524 and the upper coolers 522, which may cause a loss of convective heat.

Thus, as shown in FIG. 2, an internal temperature of the cooling portion 500 may be maintained at −10° C. by the cooler 520 disposed in the cooling portion 500. In this example, the internal temperature of the cooling portion 500 may be evenly maintained by the upper coolers 522 and the lower coolers 524.

The radiation cooling portion 600 may be provided on the cooling portion 500 to implement radiation cooling.

Although FIG. 1 illustrates the radiation cooling portion 600 disposed on the cooling portion 500, the disposition of the radiation cooling portion 600 is not limited thereto. It is obvious that the radiation cooling portion 600 may be disposed adjacent to the blocking portion 400.

The radiation cooling portion 600 may be provided in a size sufficient to cover the upper portion of the upper case 510, and disposed on the upper case 510. The radiation cooling portion 600 may be provided using stainless steel. The radiation cooling portion 600 may be covered with aluminum foil for efficient radiant heat transfer of the covering material 410 or the thermal screen 420 of the blocking portion 400.

In this example, as shown in FIG. 2, a surface temperature of the radiation cooling portion 600 may decrease to −30° C. to −40° C. Accordingly, a loss of radiant heat may occur in the cooling portion 500.

The apparatus 10 may further include a temperature measuring portion (not shown).

The temperature measuring portion may measure a temperature of the upper side of the internal case 100 and a temperature of the lower side of the internal case 100. The temperature of the upper side of the internal case 100 and the temperature of the lower side of the internal case 100 may be used to calculate an overall heat transfer coefficient in the future.

The temperature of the upper side of the internal case 100 and the temperature of the lower side of the internal case 100 may refer to the internal temperature of the internal case 100 and the external temperature of the upper side of the internal case 100, respectively.

In detail, an overall heat capacity may be calculated by measuring a quantity of heat supplied by the second temperature adjusting element 320 for a predetermined time while maintaining the internal temperature of the internal case 100 to be uniform.

As shown in FIG. 2, the overall heat capacity may be equal to a quantity of heat $Q_t$ passing through the covering material 410 and the thermal screen 420 of the blocking portion 400.

To maintain thermal equilibrium between the internal temperature of the internal case 100 and the temperature of the space between the external case 200 and the internal case 100, a quantity of heat corresponding to the quantity of heat $Q_t$ passing through the covering material 410 and the thermal screen 420 of the blocking portion 400 is to be supplied by the second temperature adjusting element 320.

Thus, hereinafter, the overall heat capacity will be regarded as the same as the quantity of heat $Q_t$ passing through the blocking portion 400.

The overall heat transfer coefficient may be calculated by dividing the overall heat capacity by the area $A_w$ of the covering material 410 or the thermal screen 420 of the blocking portion 400, and a difference between the internal temperature of the internal case 100 and the external temperature of the upper side of the internal case 100.

In this example, temperature measuring portions may be disposed at various positions. For example, the temperature measuring portions may be disposed on inner and outer side surfaces of the internal case 100, and inner and outer side surfaces of the cooling portion 500.

The apparatus 10 configured as described above may implement various covering conditions through combinations of the covering material 410 and the thermal screen 420, implement a wind velocity through the cooler 520, prevent a loss of heat through the sides of the internal case 100 by achieving thermal equilibrium between the internal temperature of the internal case 100 and the temperature of the space between the external case 200 and the internal case 100, and allow a loss of heat only through the blocking portion 400, thereby measuring an overall heat transfer coefficient more accurately and efficiently.

Hereinafter, a method of measuring an overall heat transfer coefficient according to an embodiment will be described.

Figure 3:
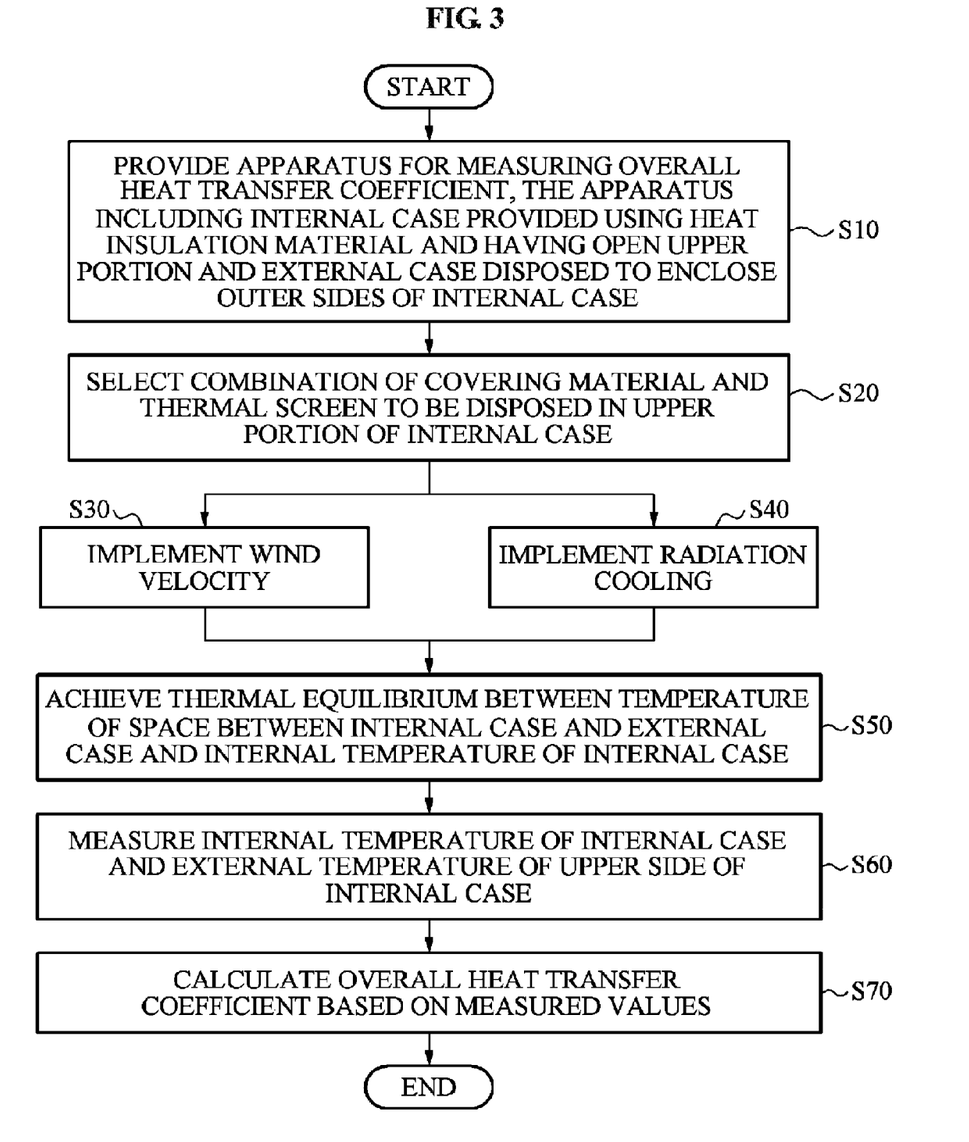
FIG. 3 is a flowchart illustrating a method of measuring an overall heat transfer coefficient according to an embodiment of the present invention.

FIG. 3 is a flowchart illustrating a method of measuring an overall heat transfer coefficient according to an embodiment of the present invention.

Referring to FIG. 3, the overall heat transfer coefficient may be measured as follows.

In operation S10, an apparatus for measuring an overall heat transfer coefficient, the apparatus including an internal case provided using a heat insulation material and having an open upper portion, and an external case disposed to enclose outer sides of the internal case, may be provided.

In this example, the internal case may be effectively sealed by the external case.

In operation S20, a combination of a covering material and a thermal screen to be disposed in an upper portion of the internal case may be selected.

Various combinations of the covering material and the thermal screen may be used to measure a heat insulation performance or a heat-retaining performance of the covering material or the thermal screen.

The selected combination of the covering material and thermal screen may be provided in the upper portion of the internal case.

After the combination of the covering material and the thermal screen are provided, a wind velocity may be implemented, in operation S30.

The wind velocity may be implemented by a cooler provided in a form of a fan. The wind velocity may change based on a rotation velocity of the fan.

In addition, after the combination of the covering material and the thermal screen is provided, radiation cooling may be implemented, in operation S40.

By disposing a radiation cooling portion above the combination of the covering material and the thermal screen, a loss of radiant heat may be caused.

In operation S50, thermal equilibrium between a temperature of a space between the internal case and the external case and an internal temperature of the internal case may be achieved by adjusting the internal temperature of the internal case and an internal temperature of the external case.

In detail, the internal temperature of the internal case and the temperature of the space between the external case and the internal case may be maintained to be uniform.

In operation S60, the internal temperature of the internal case and an external temperature of an upper side of the internal case may be measured.

In operation S70, the overall heat transfer coefficient may be calculated based on the measured values.

In detail, the overall heat transfer coefficient may be calculated as follows.

An overall heat capacity may be calculated by measuring a quantity of heat supplied by a temperature adjusting portion for a predetermined time while maintaining the internal temperature of the internal case to be uniform.

The overall heat transfer coefficient may be calculated by dividing the overall heat capacity by a surface area $A_w$ of the covering material or the thermal screen of a blocking portion, and a difference between the internal temperature of the internal case and the external temperature of the upper side of the internal case.

As described above, the method of measuring an overall heat transfer coefficient according to an embodiment may suggest a quantitative heat-retaining performance or a heat insulation performance of a covering material or a thermal screen, simply implement various covering conditions of a greenhouse, and implement a wind velocity and radiation cooling.

According to an embodiment of the present invention, an apparatus and method for measuring an overall heat transfer coefficient may suggest a quantitative heat-retaining performance or a quantitative heat insulation performance of a covering material or a thermal screen.

According to an embodiment of the present invention, an apparatus and method for measuring an overall heat transfer coefficient may measure an overall heat transfer coefficient more accurately by allowing heat to pass only through a blocking portion.

According to an embodiment of the present invention, an apparatus and method for measuring an overall heat transfer coefficient may simply implement various covering conditions of a greenhouse.

According to an embodiment of the present invention, an apparatus and method for measuring an overall heat transfer coefficient may implement a wind velocity and radiation cooling.

According to an embodiment of the present invention, an apparatus and method for measuring an overall heat transfer coefficient may establish standards of a covering material or a thermal screen for a greenhouse.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An apparatus for measuring an overall heat transfer coefficient of a covering material or a thermal screen, the apparatus comprising:
   an internal case provided using a heat insulation material and having an open upper portion;
   an external case configured to enclose outer sides excluding an upper portion of the internal case, and provided using a heat insulation material;
   a temperature adjusting portion configured to adjust an internal temperature of the external case and an internal temperature of the internal case;
   a blocking portion disposed in an upper portion of the internal case to seal the internal case; and
   a cooling portion comprising an upper case configured to extend from an outer side of the external case, and comprising a side provided using a heat insulation material, and a cooler provided on the side of the upper case,
   wherein the blocking portion is configured to implement various covering conditions through a combination of the covering material and the thermal screen,
   the overall heat transfer coefficient is calculated by dividing an overall heat capacity by an area of the covering material or the thermal screen of the blocking portion, and a difference between the internal temperature of the internal case and an external temperature of an upper side of the internal case.

2. The apparatus of claim 1, wherein the temperature adjusting portion comprises:
   a first temperature adjusting element disposed in a space between the external case and the internal case; and
   a second temperature adjusting element disposed in the internal case,
   wherein the first temperature adjusting element and the second temperature adjusting element are configured to achieve thermal equilibrium between a temperature of the space between the internal case and the external case and the internal temperature of the internal case.

3. The apparatus of claim 1, wherein the cooler comprises:
   an upper cooler disposed on an upper side in the cooling portion; and
   a lower cooler disposed on a lower side in the cooling portion,
   wherein the lower cooler is disposed adjacent to an upper portion of the blocking portion to circulate air above the blocking portion, and an operation of the lower cooler is adjusted to implement a wind velocity.

4. The apparatus of claim 1, further comprising:
   a radiation cooling portion disposed on the cooling portion to cover an upper portion of the upper case,
   wherein a surface temperature of the radiation cooling portion is decreased to occur a loss of radiant heat, thereby implementing radiation cooling.

5. The apparatus of claim 1, wherein the covering material and the thermal screen are disposed to be spaced apart from each other in an upper portion of the internal case.

6. An apparatus for measuring an overall heat transfer coefficient of a covering material or a thermal screen, the apparatus comprising:
   an internal case provided using a heat insulation material, and having an open upper portion;
   a blocking portion disposed in an upper portion of the internal case to seal the internal case and comprising the covering material or the thermal material; and
   a cooling portion disposed on the blocking portion to circulate air above the blocking portion,
   wherein the overall heat transfer coefficient is calculated by dividing an overall heat capacity by an area of the covering material or the thermal screen of the blocking portion, and a difference between the internal temperature of the internal case and an external temperature of an upper side of the internal case, the cooling portion comprises:
   an upper case configured to extend from an outer side of the external case, and comprising a side provided using a heat insulation material; and
   a cooler provided on the side of the upper case,
   wherein operations of the cooler is controlled to adjust wind velocity conditions.

7. The apparatus of claim 6, further comprising:
an external case provided using a heat insulation material, and configured to seal the internal case, the blocking portion, and the cooling portion.

8. The apparatus of claim 7, further comprising:
a temperature adjusting portion,
wherein the temperature adjusting portion comprises:
   a first temperature adjusting element disposed in a space between the external case and the internal case; and
   a second temperature adjusting element disposed in the internal case, and
   the first temperature adjusting element and the second temperature adjusting element are configured to achieve thermal equilibrium between a temperature of the space between the internal case and the external case and an internal temperature of the internal case.

9. The apparatus of claim 6, further comprising:
   a radiation cooling portion provided on the internal case to seal the internal case,
   wherein a surface temperature of the radiation cooling portion is decreased to occur a loss of radiant heat, thereby implementing radiation cooling.

10. A method of measuring an overall heat transfer coefficient of a covering material or a thermal screen, the method comprising:
   providing an apparatus for measuring an overall heat transfer coefficient, the apparatus comprising an internal case provided using a heat insulation material and having an open upper portion, and an external case configured to enclose outer sides of the internal case;

selecting a combination of the covering material and the thermal screen to be disposed in an upper portion of the internal case;

achieving thermal equilibrium between a temperature of a space between the internal case and the external case and an internal temperature of the internal case;

measuring the internal temperature of the internal case and an external temperature of an upper side of the internal case; and calculating the overall heat transfer coefficient based on the measured values, wherein the overall heat transfer coefficient is calculated by dividing an overall heat capacity by an area of the covering material or the thermal screen, and a difference between the internal temperature of the internal case and the external temperature of the upper side of the internal case, the apparatus for measuring an overall heat transfer coefficient further comprises a cooling portion comprising an upper case configured to extend from an outer side of the external case, and comprising a side provided using a heat insulation material, and a cooler provided on the side of the upper case.

11. The method of claim 10, further comprising:

implementing a wind velocity or radiation cooling, wherein the wind velocity is implemented by controlling an operation of the cooler, the radiation cooling is implemented by decreasing a surface temperature of a radiation cooling portion disposed on the cooling portion to occur a loss of radiant heat of the covering material or the thermal screen.

\* \* \* \* \*